United States Patent
Kanayama et al.

(10) Patent No.: US 10,441,631 B2
(45) Date of Patent: Oct. 15, 2019

(54) THERAPEUTIC AGENT FOR AMNIOTIC FLUID EMBOLISM

(71) Applicant: CSL BEHRING GMBH, Marburg (DE)

(72) Inventors: Naohiro Kanayama, Hamamutsu (JP); Tomoaki Ikeda, Tshu (JP); Madoka Furuhashi, Nagoya (JP)

(73) Assignee: CSL BEHRING GMBH, Marburg (DE)

( * ) Notice: Subject to any disclaimer, the term of this patent is extended or adjusted under 35 U.S.C. 154(b) by 263 days.

(21) Appl. No.: 14/771,090

(22) PCT Filed: Feb. 28, 2014

(86) PCT No.: PCT/EP2014/053902
§ 371 (c)(1),
(2) Date: Aug. 27, 2015

(87) PCT Pub. No.: WO2014/131865
PCT Pub. Date: Sep. 4, 2014

(65) Prior Publication Data
US 2016/0008425 A1    Jan. 14, 2016

(30) Foreign Application Priority Data
Feb. 28, 2013  (JP) ................................ 2013-038170
Apr. 10, 2013  (EP) .................................. 13163205

(51) Int. Cl.
*A61K 38/17*   (2006.01)
*A61K 38/57*   (2006.01)
*A61K 9/00*    (2006.01)
*A61K 9/08*    (2006.01)

(52) U.S. Cl.
CPC ........ *A61K 38/1709* (2013.01); *A61K 9/0019* (2013.01); *A61K 38/57* (2013.01)

(58) Field of Classification Search
None
See application file for complete search history.

(56) References Cited

U.S. PATENT DOCUMENTS

| | | |
|---|---|---|
| 5,939,389 A | 8/1999 | Eisele et al. |
| 6,248,365 B1 | 6/2001 | Römisch et al. |
| 7,053,176 B1 | 5/2006 | Häfner et al. |
| RE43,691 E * | 9/2012 | Nuijens ........................ 514/20.1 |

FOREIGN PATENT DOCUMENTS

| | | |
|---|---|---|
| WO | WO 01/79271 A1 | 10/2001 |
| WO | WO 2007/073186 A2 | 6/2007 |
| WO | WO 2013/041677 A1 | 3/2013 |

OTHER PUBLICATIONS

Burtelow, M., et al. 2007 Transfusion 47: 1564-1572.*
Dickneite, G. 1993 Behring Inst Mitt 93: 299-305.*
Gist, R.S., et al. 2009 Anesth Analg 108: 1599-1602.*
Davies, S. 2001 Canadian Journal of Anaesthesia 48(1): 88-98.*
Taenaka, N., et al. 1981 Anaesthesia 36: 389-393. (Year: 1981).*
English translation of Kanayama et al., "3) Massive bleeding during delivery (1) Amniotic fluid embolism", Acta Obstetrica et Gynaecologica Japonica, vol. 64, No. 9, Sep. 2012, pp. N-407-N-411.
International Search Report issued in PCT/EP2014/053902, dated Apr. 22, 2014.
Kanayama et al., "3) Massive bleeding during delivery (1) Amniotic fluid embolism", Acta Obstetrica et Gynaecologica Japonica, vol. 64, No. 9, Sep. 2012, pp. N-407-N-411.
Kanayama et al., "Maternal death analysis from the Japanese autopsy registry for recent 16 years: significance of amniotic fluid embolism", The Journal of Obstetrics and Gynaecology Research, vol. 37, No. 1, Jan. 2011, pp. 58-63.
Thongrong et al., "Amniotic fluid embolism", International Journal of Critical Illness and Injury Science, vol. 3, Issue 1, Jan.-Mar. 2013, pp. 51-57.
Written Opinion issued in PCT/EP2014/053902, dated Apr. 22, 2014.
Itakura, "Transfusion method for obstetric DIC hemostasis," Sanka to Fujinnka (Obstetrics and Gynecology), vol. 77, No. 6, 2010, pp. 703-708 (9 pages total), with a partial English translation.
Yonemasu et al., "C1 Inhibitor," Nippon Rinsho (Japanese Clinical), vol. 48, 1990, pp. 402-406 (7 pages total), with a partial English translation.

* cited by examiner

*Primary Examiner* — Marsha Tsay
(74) *Attorney, Agent, or Firm* — Birch, Stewart, Kolasch & Birch, LLP

(57) ABSTRACT

The present invention relates to a therapeutic agent for amniotic fluid embolism (AFE). Furthermore, the present invention relates to a therapeutic agent for AFE comprising a C1-inhibitor, particularly a human plasma-derived C1-inhibitor.

21 Claims, 1 Drawing Sheet

THERAPEUTIC AGENT FOR AMNIOTIC FLUID EMBOLISM

CROSS REFERENCE TO RELATED APPLICATIONS

This application is the National Phase of PCT International Application No. PCT/EP2014/053902, filed on Feb. 28, 2014, which claims priority under 35 U.S.C. 119(a) to Patent Application No. 2013-038170, filed in Japan on Feb. 28, 2013, and to patent application Ser. No. 13/163,205.1, filed in Europe on Apr. 10, 2013, all of which are hereby expressly incorporated by reference into the present application.

TECHNICAL FIELD TO WHICH THE INVENTION BELONGS

The present invention relates to a therapeutic agent for amniotic fluid embolism (AFE). Furthermore, the present invention relates to a therapeutic agent for AFE comprising a C1-inhibitor, particularly a human plasma-derived C1-inhibitor.

TECHNICAL BACKGROUND

Amniotic fluid embolism (AFE) is defined as a disease accompanied by pathological conditions of a pulmonary hypertension caused by obstruction of pulmonary capillary and of a cardiorespiratory failure therefrom, which are induced by inflow of amniotic fluid into maternal blood. Recently, not only an embolism by amniotic fluid but also an anaphylactoid reaction by amniotic fluid components has been indicated as a cause of AFE. Incidence of AFE is rare, but when once it occurs, it leads to a life-threatening status, such as maternal death, in a short time (see, Non-patent document 1, 2).

AFE is classified to two categories; one is established AFE which is confirmed by a histopathological examination after autopsy, and another one is potential AFE which meets three of the following diagnostic criteria for AFE:

Diagnostic criteria for potential AFE:
(1) Developed during pregnancy or within 12 hours after delivery;
(2) Intensive medical treatment to one or more of the symptoms or diseases below:
   (a) cardiac arrest,
   (b) massive bleeding of unknown cause within 2 hours after delivery,
   (c) disseminated intravascular coagulation (DIC),
   (d) respiratory failure,
(3) Observed findings and symptom cannot be explained by the other diseases (see, Non-patent document 1).

Further, serological method can be also employed as a supplementary diagnosis for AFE. The method aims to detect a specific substance derived from amniotic fluid or meconium in maternal blood. Zinc coproporphirin 1 (Zn-CP1) and sialyl Tn (STN) can be used for the purpose (see, Non-patent document 1).

For treatment of AFE, anti-shock therapy (such as, airway opening, blood vessel securing, fluid replacement, administration of anti-shock agent) and anti-DIC therapy (such as, administrations of antithrombin and/or fresh frozen plasma (FFP)) have been basically employed. However, as the mortality rate is still high, further effective therapeutic method for AFE has been strongly desired in addition to these conventional therapeutic methods.

On the other hand, regarding involvement of complement system in pathophysiology of AFE, it has been reported that complements C3 and C4 are decreased in maternal blood of patients with DIC, but no report has been made on the involvement of C1-inhibitor in AFE.

Therefore, there has been no description or suggestion on the use of C1-inhibitor for the treatment of AFE.

NON-PATENT DOCUMENTS

Non-patent document 1 Kanayama N et al., "3) Massive bleeding during delivery (1) Amniotic fluid embolism", Acta Obstetrica et Gynaecologica Japonica, September 2012, Vol. 64, No. 9, N-407 to 411;

Non-patent document 2 Kanayama N et al., "J. Obstet. Gynaecol. Res., 2011 January; 37(1):58-63, "Maternal death analysis from the Japanese autopsy registry for recent 16 years: significance of amniotic fluid embolism".

SUMMARY OF THE INVENTION

The technical problem to be solved by the invention was to provide a therapeutically effective agent for amniotic fluid embolism.

The solution to this technical problem is achieved by providing the embodiments characterized in the claims.

Accordingly, the inventors have investigated further effective agents for treatment of AFE and found significant decrease of C1-inhibitor activity in the patient's bloods in comparison with that of normal pregnant women. And then therapeutic effect of C1-inhibitor was clinically demonstrated in a patient of potential AFE, and thereby the present invention has been completed.

Namely, the present invention is summarized as a provision of a therapeutic agent for AFE comprising a C1-inhibitor as an active ingredient, more specifically a provision of a therapeutic agent for AFE comprising human C1-inhibitor, and further specifically a provision of a therapeutic agent for AFE comprising human plasma-derived C1 inactivator, i.e. human plasma-derived C1 inhibitor.

The therapeutic agent of the present invention has an advantageous in term of life-saving effect etc. in comparison with the conventional therapeutic methods for amniotic fluid embolism.

Figure 1:
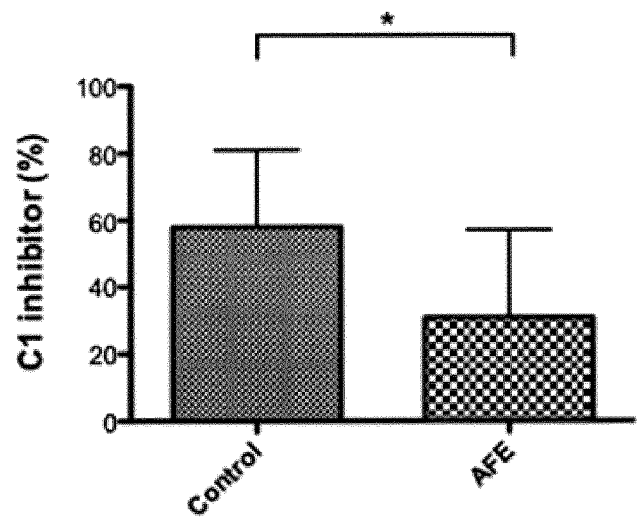
FIG. 1

It shows results of comparative measurements of C1-inhibitor activity in sera at the delivery between control group consisting of normal pregnant women and potential AFE patients group. Mean value and standard deviation are represented therein. Symbol "*" means presence of significant difference of $p<0.01$.

FIG. 2

It shows results of the comparative measurement as above by distribution of individual data in each group. The values less than 25% are treated as 25%. Mean values and standard deviations are represented by the longer horizontal bars in the middle and two shorter horizontal bars upside and downside, respectively. Symbol "*" means presence of significant difference of $p<0.01$.

DETAILED DESCRIPTION OF THE INVENTION

C1-inhibitor is also referred to as C1 esterase inhibitor or C1-INH, and is a glycoprotein consisting of 478 amino acids, which belongs to a superfamily of serine protease inhibitors which are collectively referred to as serpins. Its designation originates from the initial description as the only known physiological inhibitor of the classical complement pathway in blood and tissue. However, C1-inhibitor is also a major regulator of the kallikrein-kinin system (KKS) by blocking FXIIa and plasma kallikrein. Apart from several other functions (e.g. FXIa inhibition), it is the only known physiological inhibitor of C1s and C1r, the activated homologous serine proteases of the first component of the complement system.

According to the present invention the terms "C1-inhibitor" refers to the proteins or fragments thereof that function as serine protease inhibitors to inhibit proteases associated with the complement system, preferably proteases C1r and C1s as well as MASP-1 and MASP-2, with the kallikrein-kinin system (KKS), preferably plasma kallikrein and FXIIa, and with the coagulation system, preferably FXIa. In addition, C1-inhibitor can serve as an anti-inflammatory molecule that reduces the selectins-mediated leukocyte adhesion to endothelial cells. "C1-inhibitor" as used here can be a native serine protease inhibitor or active fragment thereof, or it can comprise a recombinant peptide, a synthetic peptide, peptide mimetic, or peptide fragment that provides similar functional properties—e.g., the inhibition of proteases C1r and C1s, and/or MASP-1 and MASP-2 and/or FXIIa and/or FXIa. For further disclosure regarding the structure and function of C1-inhibitor, see U.S. Pat. Nos. 5,939,389; 6,248,365; 7,053,176; and WO 2007/073186.

Therefore, in a preferred embodiment of the present invention, C1-inhibitor is a plasma-derived or a recombinant C1-inhibitor. In a further preferred embodiment the C1-inhibitor is the naturally occurring human protein or a variant thereof. The C1-inhibitor shall encompass all natural occurring alleles which have the same function as the C1-inhibitor. In the most preferred embodiment said inhibitor is the human C1 esterase Inhibitor.

In another preferred embodiment the C1-inhibitor according to the present invention is modified to improve bioavailability and/or half-life, to improve efficacy and/or to reduce potential side effects. The modification can be realized by recombinant or other steps. Examples for such a modification could be a glycosylation or an albumin fusion of the described C1-inhibitor. For further disclosure regarding the glycosylation and the albumin fusion of proteins see WO 01/79271.

In various embodiments, C1-inhibitor can be produced according to methods known to one of skill in the art. For example, plasma-derived C1-inhibitor can be prepared by collecting blood plasma from several donors. Donors of plasma should be healthy as defined in the art. Preferably, the plasma of several (1000 or more) healthy donors is pooled and optionally further processed. An exemplary process for preparing C1-inhibitor for therapeutic purposes is disclosed in U.S. Pat. No. 4,915,945. Alternatively, in some embodiments C1-inhibitor can be collected and concentrated from natural tissue sources using techniques known in the art. Commercially available products comprising C1-inhibitor are, e.g. plasma-derived Cinryze® (Viropharma), recombinant Ruconest® or Rhucin® (both Pharming), and plasma-derived Berinert® (CSL Behring). Berinert® is indicated for treatment of hereditary angioedema and congenital deficiencies. Recombinant C1-inhibitor can be prepared by known methods.

In certain embodiments, a pharmaceutical composition comprising C1-inhibitor is prepared for use in the treatment of amniotic fluid embolism. Methods of formulating pharmaceutical compositions comprising C1-inhibitor are known in the art. For example, if a powder or lyophilized form of C1-inhibitor (e.g., by freeze drying) is provided and an aqueous pharmaceutical is desired, the powder can be dissolved by mixing with aqueous components of the pharmaceutical formulation and stirred using suitable techniques such as vortexing or gentle agitation. In other embodiments, C1-inhibitor is provided in lyophilized form and combined with aqueous pharmaceutical components (e.g., additional active components or inactive components such as fillers, stabilizers, solvents, or carriers) prior to administration.

In certain embodiments, a pharmaceutical composition can comprise at least one additive such as a filler, bulking agent, buffer, stabilizer, or excipient. Standard pharmaceutical formulation techniques are well known to persons skilled in the art (see, e.g., 2005 *Physicians' Desk Reference®*, Thomson Healthcare: Montvale, N.J., 2004; *Remington: The Science and Practice of Pharmacy*, 20th ed., Gennado et al., Eds. Lippincott Williams & Wilkins: Philadelphia, Pa., 2000). Suitable pharmaceutical additives include, e.g., mannitol, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In certain embodiments, the pharmaceutical compositions may also contain pH buffering reagents and wetting or emulsifying agents. In further embodiments, the compositions may contain preservatives or stabilizers.

The formulation of pharmaceutical compositions may vary depending on the intended route of administrations and other parameters (see, e.g., Rowe et al., *Handbook of Pharmaceutical Excipients*, 4th ed., APhA Publications, 2003). In some embodiments, the pharmaceutical composition may be a lyophilized cake or powder. The lyophilized composition may be reconstituted for administration by intravenous injection, for example with Sterile Water for Injection, USP. In other embodiments, the composition may be a sterile, non-pyrogenic solution. In still further embodiments, the composition is delivered in powder form in a pill or tablet.

The described pharmaceutical compositions may comprise C1-inhibitor as the sole active compounds or may be delivered in combination with at least one other compound, composition, or biological material. Examples of such compounds include vitamins, antibiotics, or compounds intended to remove or inhibit blood clot formation in the tissue (e.g., tissue plasminogen activator, acetylsalicylic acid, clopidogrel, or dipyridamole).

Also disclosed are kits for the treatment of amniotic fluid embolism. In certain embodiments, the kits comprise (a) C1-inhibitor, (b) instructions for use in the treatment of amniotic fluid embolism and optionally (c) at least one further therapeutically active compound or drug. The C1-inhibitor component may be in liquid or solid form (e.g. after lyophilization). If in liquid form, the C1-INH may comprise additives such as stabilizers and/or preservatives such as proline, glycine, or sucrose or other additives that enhance shelf-life.

In certain embodiments, the kit may contain additional compounds such as therapeutically active compounds or drugs that are to be administered before, at the same time or after administration of the C1-inhibitor. Examples of such compounds include vitamins, antibiotics, anti-viral agents, etc. In other embodiments, compounds intended to remove or inhibit blood clot formation in the tissue (e.g., tissue plasminogen activator, acetylsalicylic acid, clopidogrel, or dipyridamole) can be included with the kit.

In various embodiments, instructions for use of the kits will include directions to use the kit components in the treatment of amniotic fluid embolism. The instructions may further contain information regarding how to prepare (e.g. dilute or reconstitute, in the case of freeze-dried protein) the C1-Inhibitor. The instructions may further include guidance regarding the dosage and frequency of administration.

A formulation of the C1-inhibitor can be delivered to the individual by any pharmaceutically suitable means of administration. Various delivery systems are known and can be used to administer the composition by any convenient route. In a preferred embodiment the formulation of the C1-inhibitor is administered systemically. For systemic use, the therapeutic protein is formulated for parenteral or enteral (e.g., oral, vaginal or rectal) delivery according to conventional methods. A parenteral administration may include, without limitation, intravenous, subcutaneous, intramuscular, intraperitoneal or by an injection directly into the tissue, intrapulmonar, transdermal or intranasal administration. The most preferential route of administration is intravenous administration. The formulations can be administered continuously by infusion or by bolus injection. Some formulations encompass slow release systems.

A formulation of C1-inhibitor may be administrated to a patient for the treatment of amniotic fluid embolism in therapeutically effective timing and frequency. The timing and frequency of administration may be determined by a physician according to the age, general condition and the severity of the medical condition in the patient.

In certain embodiments regarding the treatment of amniotic fluid embolism the formulation of the C1-inhibitor is administered in therapeutic effective amounts within 5, 10, 15, 20, 30, or 45 minutes, or 1, 2 or 3 hours after the onset of clinically potential amniotic fluid embolism. Preferably, the formulation of C1-inhibitor is administered within 5, 10 or 15 minutes after the onset of clinically potential amniotic fluid embolism, and most preferably it is administered directly after the onset (or at any time in between).

Furthermore, the formulation of the C1-inhibitor may be administered in a single dose or further in additional doses, as determined by a physician, i.e. Administration to a patient may occur in a single dose or in repeated administrations, and in any of a variety of physiologically acceptable salt forms, and/or with an acceptable pharmaceutical carrier and/or additive as part of a pharmaceutical composition. Therefore in certain embodiments the C1-inhibitor is administered (i) in a single dose as injection or infusion, or (ii) in multiple doses, preferably in two doses, each as injection or infusion, or (iii) as a long-term infusion or application. The long-term-infusion/application is administered over a period of time, preferably over a period of 30 minutes to 3 hours, more preferably 30 minutes to 2 hours, more preferably 30 minutes to 1 hour (or any time period in between).

The composition comprising C1-inhibitor may be administered to a patient in therapeutically effective amounts. Generally, a therapeutically effective amount may vary with the subject's age, general condition and the severity of the medical condition in the subject. The dosage may be determined by a physician and adjusted, as necessary, to suit the observed effects of the treatment. In certain embodiments, the dose of C1-inhibitor is 1, 5, 7.5, 10, 15, 20, 25, 30, 50, 75, 100, 125, 150, 175, 200, 225, 250, 275, 300, 325, 350, 375, 400, 450, 500, or 1000 U/kg of bodyweight (or any value in between). Exemplary therapeutic ranges for C1-INH administration are also disclosed in U.S. Pat. No. 5,939,389. Preferably the C1-inhibitor is administered in a dose of 5 to 500 units per kg body weight, more preferably 10 to 200 units per kg body weight, and most preferably in a dose of 20 to 100 units per kg body weight.

A pharmaceutical containing human plasma-derived C1-inhibitor as an active ingredient was approved in German in 1979 and has been marketed as a therapeutic agent of hereditary angioedema (HAE). Then after, it has been approved and marketed in many countries. In Japan, it was also approved in 1990 for treatment of acute attack in HAE and has been marketed under the product name "Berinert® P I.V. Injection 500". One vial of the product comprises 500-folds or more of human C1-inhibitor contained in 1 mL of healthy donor plasma (CSL Behring KK., Pharmaceutical interview form "Plasma fractionation formulation (lyophilized human C1 inactivator concentrate) Berinert® P I.V. Injection 500", March 2012 (the revised $4^{th}$ edition)).

The present inventors had tried to measure C1-inhibitor activity in potential AFE patients and revealed for the first time that the C1-inhibitor activity is decreased in sera of AFE patients at the delivery, taking into account the facts that complement C3 and C4 are decreased in maternal blood of AFE with DIC and that C1-inhibitor is an important biologically defensive substance inhibiting complement C1, C3, FXII, classical complement system and bradykinin and acting on immune system, vascular permeability and coagulation-fibrinolysis system, and decrease of C1-inhibitor activity leads to development of angioedema, The inventors consider that said decrease of C1-inhibitor activity in sera of AFE patients at the delivery arises from excessive consumption of C1-inhibitor by enhancement of complement system in mother body. C1-inhibitor was administered clinically to treat a potential AFE patient and a desired therapeutic effect was successfully obtained.

The present invention is concretely explained by the following examples.

Example 1: Study of C1-Inhibitor Activity in Potential AFE

Method

Sera at the delivery were collected, under informed consent, from 40 normal pregnant women as a control group (ages: 31±5.1; gestation periods: 273±11 days; amount of bleeding at the delivery: 590±367 mL), and 57 patients diagnosed as potential AFE (ages: 34±4.5; gestation periods: 267±19 days; amount of bleeding at the delivery: 4489±2900 mL). C1-inhibitor activities in sera were determined by a method using chromogenic synthetic substrate. Standard value of C1-inhibitor activity in serum is 70 to 130%, detection limit is 25%, and the values less than 25% were treated uniformly as 25%. Obtained results of each group were compared to each other by Mann-Whitney test.

Results

Figure 2:
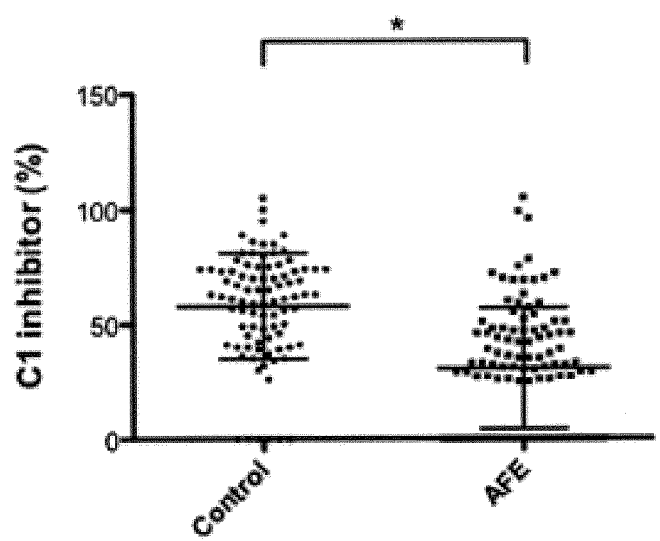

The C1-inhibitor activities in sera at the delivery were 53±21.0% in control group and 35.5±13.5% in potential AFE group. Significant difference (p<0.01) exists between both groups. The values in potential AFE group were significantly low in comparison with that of control group (FIG. 1). Furthermore, when comparing individual data, the number of cases less than 25% of detection limit were 4 (10%) in control group while 19 (33.3%) in potential AFE group, wherein significant difference exists between both groups (FIG. 2).

Conclusion

It is shown that C1-inhibitor activities are decreased in sera at the delivery. Such decrease of C1-inhibitor activity suggests a possible involvement thereof in the induction of DIC type bleeding after delivery in AFE, since C1-inhibitor regulates not only complement system but also kinin production system and coagulation-fibrinolysis system.

Example 2: Treatment of Potential AFE with C1-Inhibitor

One postpartum woman (age 34, gestation period 40 weeks), who had cervical laceration and whose uterine bleeding was not stopped even after the suture, was transported by ambulance and diagnosed as potential AFE and treated at the maternal-fetal intensive care unit (MFICU) as follows.

Amount of bleeding till the arrival by ambulance was not recorded, but it was estimated to be rather large from hemoglobin (Hb) of 2.6 g/dL and consciousness level of JCSII-10 to II-20 in Japanese Coma Scale. After transporting into MFICU, the consciousness level was reduced to JCSIII-300 and arose atonic uterine bleeding, to whom mass infusion containing oxytocin was started. Since spontaneous breathing was shallow, manual ventilation with a mask was conducted. Intubation was made and manual ventilation control was continued. Then, transfusions of fresh frozen plasma (FFP) and red cell concentrate (RCC) were started when accumulated amount of bleeding was 2934 g from the arrival. Noradrenalin was sequentially administered. Due to massive bleeding from uterus, transfusion of platelet concentrate (PC) was started. At that time, diameters of both left and right pupils were 6 mm with no light reflex, accumulated amount of bleeding was 4310 g and non-coagulable bleeding continued.

Then, 2 vials of a C1-inhibitor product (Berinert® P I.V. 500, CSL Behring KK) were intravenously administered and subsequently 3 vials of fibrinogen products were intravenously administered. Soon after the administration of C1-inhibitor product, improvement of level of consciousness was observed. As well, the diameters of both left and right pupils became 5 mm and light reflex in pupils was observed, which had once not been detected. Furthermore, the amount of atonic bleeding, which had once not been stopped, was reduced, and blood coagulation was also observed. Total amounts of transfusion were 20 units of RCC, 50 units of FFP and 50 units of PC. Whole measurable amount of bleeding reached to 4811 g. The patient was transported to ICU and next morning gauze pressing in uterus was removed but the bleeding was within the normal range. Artificial ventilation control was continued because of development of pulmonary edema. However the condition of patient thereafter was good, and then tube was removed and the patient was transported from ICU to MFICU on day 3, and she could be moved from the hospital on day 7.

The results suggest strongly effectiveness of C1-inhibitor in the treatment of amniotic fluid embolism.

The invention claimed is:

1. A method for the treatment of amniotic fluid embolism comprising administering to a subject in need thereof a therapeutically effective amount of a pharmaceutical composition including human plasma-derived C1 esterase inhibitor to treat amniotic fluid embolism,
wherein the pharmaceutical composition comprises human plasma-derived C1 esterase inhibitor in a concentration higher than that present in normal human plasma,
wherein the human plasma-derived C1 esterase inhibitor is administered as the sole active compound.

2. The method according to claim 1, wherein the human plasma-derived C1 esterase inhibitor is administered intravenously or subcutaneously.

3. The method according to claim 1, wherein the human plasma-derived C1 esterase inhibitor is administered in a dose of 1 to 1000 units per kg body weight.

4. The method according to claim 1, wherein the human plasma-derived C1 esterase inhibitor is administered in a single dose as an injection or as an infusion.

5. The method according to claim 1, wherein the human plasma-derived C1 esterase inhibitor is administered within 2 hours after the onset of clinically potential amniotic fluid embolism.

6. The method according to claim 1, wherein the human plasma-derived C1 esterase inhibitor is administered in a dose of 5 to 500 units per kg body weight.

7. The method according to claim 1, wherein the human plasma-derived C1 esterase inhibitor is administered in two doses, each as an injection or as an infusion.

8. The method according to claim 1, wherein the human plasma-derived C1 esterase inhibitor is administered in multiple doses, each as an injection or as an infusion.

9. The method according to claim 1, wherein the human plasma-derived C1 esterase inhibitor is administered as a long term infusion or application.

10. The method according to claim 1, wherein the human plasma-derived C1 esterase inhibitor is administered within 1 hour after the onset of clinically potential amniotic fluid embolism.

11. The method according to claim 1, wherein the human plasma-derived C1 esterase inhibitor is administered within 30 minutes after the onset of clinically potential amniotic fluid embolism.

12. The method according to claim 1, wherein the human plasma-derived C1 esterase inhibitor is administered directly after the onset of clinically potential amniotic fluid embolism.

13. The method according to claim 1, wherein the pharmaceutical composition includes human plasma-derived C1 esterase inhibitor in a concentration at least 50 times higher than that present in normal human plasma.

14. The method according to claim 1, wherein the human plasma-derived C1 esterase inhibitor is administered intravenously.

15. The method according to claim 14, wherein the human plasma-derived C1 esterase inhibitor is administered in a dose of 10 to 200 units per kg body weight.

16. A method for treatment of amniotic fluid embolism comprising administering to a subject in need thereof a therapeutically effective amount of a pharmaceutical composition including human plasma derived C1 esterase inhibitor to treat amniotic fluid embolism,
wherein the pharmaceutical composition comprises human plasma derived C1 esterase inhibitor in a concentration higher than that present in normal human plasma, and
wherein the human plasma derived C1 esterase inhibitor is administered within 3 hours after the onset of clinically potential amniotic fluid embolism,
wherein the human plasma derived C1 esterase inhibitor is administered as the sole active compound.

17. A method for treatment of amniotic fluid embolism comprising administering to a subject in need thereof a therapeutically effective amount of a pharmaceutical composition including recombinant human C1 esterase inhibitor to treat amniotic fluid embolism, wherein the pharmaceutical composition comprises recombinant human C1 esterase inhibitor in a concentration higher than that present in normal human plasma, wherein the recombinant human C1 esterase inhibitor is administered as the sole active compound.

18. The method according to claim 17, wherein the recombinant human C1 esterase inhibitor is administered within 3 hours after the onset of clinically potential amniotic fluid embolism.

19. The method according to claim 1, wherein the human plasma-derived C1 esterase inhibitor is administered as a monotherapy.

20. The method according to claim 16, wherein the human plasma-derived C1 esterase inhibitor is administered as a monotherapy.

21. The method according to claim 17, wherein the recombinant human C1 esterase inhibitor is administered as a monotherapy.

* * * * *